(12) United States Patent
Trogolo et al.

(10) Patent No.: US 6,436,422 B1
(45) Date of Patent: Aug. 20, 2002

(54) ANTIBIOTIC HYDROPHILIC POLYMER COATING

(75) Inventors: Jeffrey A. Trogolo, Boston, MA (US); John E. Barry, Derry, NH (US)

(73) Assignee: Agion Technologies L.L.C., Wakefield, MA (US)

( * ) Notice: Subject to any disclaimer, the term of this patent is extended or adjusted under 35 U.S.C. 154(b) by 0 days.

(21) Appl. No.: 09/197,815

(22) Filed: Nov. 23, 1998

(51) Int. Cl.[7] .......................... A01N 25/00; A01N 25/34
(52) U.S. Cl. .................... 424/405; 424/404; 424/421; 424/490
(58) Field of Search ................... 424/405, 404, 424/421, 490

(56) References Cited

U.S. PATENT DOCUMENTS

| | | | |
|---|---|---|---|
| 4,775,585 A | 10/1988 | Hagiwara et al. | 428/323 |
| 4,906,464 A | 3/1990 | Yamamoto et al. | 424/78 |
| 4,911,898 A | 3/1990 | Higiwara et al. | 423/118 |
| 4,911,899 A | 3/1990 | Hagiwara et al. | 423/118 |
| 4,923,450 A | 5/1990 | Maeda et al. | 604/265 |
| 4,938,955 A | 7/1990 | Niira et al. | 424/79 |
| 4,938,958 A | 7/1990 | Niira et al. | 424/79 |
| 5,009,898 A | 4/1991 | Sakuma et al. | 424/618 |
| 5,019,096 A | 5/1991 | Fox, Jr. et al. | 623/1 |
| 5,100,671 A | 3/1992 | Maeda et al. | 424/443 |
| 5,102,401 A | 4/1992 | Lambert et al. | 604/264 |
| 5,157,005 A | 10/1992 | Suppiah | 502/62 |
| 5,180,585 A | 1/1993 | Jacobson | 424/405 |
| 5,244,667 A | 9/1993 | Hagiwara et al. | 424/409 |
| 5,296,238 A | 3/1994 | Sugiura et al. | 424/604 |
| 5,305,827 A | 4/1994 | Steele et al. | 165/133 |
| 5,405,644 A | 4/1995 | Ohsumi et al. | 427/2.31 |
| 5,441,717 A | 8/1995 | Ohsumi et al. | 423/306 |
| 5,474,797 A | 12/1995 | Sioshansi et al. | 427/2.24 |
| 5,492,763 A | 2/1996 | Barry et al. | 428/457 |
| 5,509,899 A | 4/1996 | Fan et al. | 604/96 |
| 5,520,664 A | 5/1996 | Bricault, Jr. et al. | 604/265 |
| 5,556,699 A | 9/1996 | Nirra et al. | 428/323 |
| 5,562,872 A | 10/1996 | Watanabe | 264/145 |
| 5,697,203 A | 12/1997 | Niwa | 53/510 |
| 5,698,229 A | 12/1997 | Ohsumi et al. | 424/604 |
| 5,714,430 A | 2/1998 | Gehrer et al. | 502/347 |
| 5,714,445 A | 2/1998 | Trinh et al. | 510/103 |
| 5,723,110 A | 3/1998 | Yamamoto et al. | 424/65 |
| 5,753,251 A | 5/1998 | Burrell et al. | 424/426 |
| 5,770,255 A | 6/1998 | Burrell et al. | 427/2.1 |
| 5,800,412 A | * 9/1998 | Zhang et al. | 604/280 |
| 6,013,275 A | * 1/2000 | Konagaya | 424/443 |

FOREIGN PATENT DOCUMENTS

| | | |
|---|---|---|
| EP | 781 566 A2 | 7/1997 |
| JP | 05154174 | 6/1993 |

OTHER PUBLICATIONS

HCAPLUS 1998:361053 to JP 10152579 A2, Jun. 1998.*
Derwent abstract of JP 9100205, Apr. 15, 1997.

* cited by examiner

*Primary Examiner*—Bennett Celsa
(74) *Attorney, Agent, or Firm*—Edward K. Welch, II

(57) ABSTRACT

The invention relates to an antibiotic coated substrate having an antibiotic coating composition coated thereon. The coating composition is formed of a hydrophilic polymer having antibiotic ceramic particles, preferably antibiotic zeolite, dispersed therein. The antibiotic zeolite may further comprise a discoloration agent. Another embodiment of the invention is an article comprising a substrate on which is coated the antibiotic hydrophilic coating composition. A method for preparing the antibiotic hydrophilic polymer coating on a substrate is also provided.

18 Claims, 1 Drawing Sheet

ANTIBIOTIC HYDROPHILIC POLYMER COATING

FIELD OF THE INVENTION

This invention relates to hydrophilic polymer coatings having antimicrobial properties.

BACKGROUND OF THE INVENTION

A number of metal ions have been shown to possess antibiotic activity, including silver, copper, zinc, mercury, tin, lead, bismutin, cadmium, chromium and thallium ions. It is theorized that these antibiotic metal ions exert their effects by disrupting respiration and electron transport systems upon absorption into bacterial or fungal cells. Antimicrobial metal ions of silver, copper, zinc, and gold, in particular, are considered safe for in vivo use. Antimicrobial silver ions are particularly useful for in vivo uses due to the fact that they are not substantially absorbed into the body.

Silver ions have been impregnated in the surfaces of medical implants, as described in U.S. Pat. No. 5,474,797. Silver ions have also been incorporated in catheters, as described in U.S. Pat. No. 5,520,664. The products described in these patents, however, do not exhibit an antibiotic effect for a prolonged period of time because a passivation layer typically forms on the silver ion coating. This layer reduces the release rate of the silver ions from the product, resulting in lower antibiotic effectiveness. In addition, the layer containing the silver frequently becomes discolored, causing the products to have a poor appearance. The discoloration is caused by a high flux release rate of silver ion into the surroundings.

Antibiotic zeolites can be prepared by replacing all or part of the ion-exchangeable ions in zeolite with antibiotic metal ions, as described in U.S. Pat. Nos. 4,011,898; 4,938,955; 4,906,464; and 4,775,585. Polymers incorporating antibiotic zeolites have been used to make refrigerators, dish washers, rice cookers, plastic film, chopping boards, vacuum bottles, plastic pails, and garbage containers. Other materials in which antibiotic zeolites have been incorporated include flooring, wall paper, cloth, paint, napkins, plastic automobile parts, bicycles, pens, toys, sand, and concrete. Examples of such uses are described in U.S. Pat. Nos. 5,714,445; 5,697,203; 5,562,872; 5,180,585; 5,714,430; and 5,102,401.

Hydrophilic coatings with low friction have been applied to medical devices such as catheters. See, for example, U.S. Pat. No. 5,509,899. Such coatings are highly desirable to allow for easy insertion into the body. Hydrophilic coatings, however, are excellent breeding grounds for bacteria.

U.S. Pat. No. 4,923,450 discloses a catheter having a coating of antibiotic zeolite. U.S. Pat. No. 5,100,671 describes a medical article that is formed using silicone rubber that contains antibiotic zeolite. However, use of conventional antibiotic zeolite, such as that described in U.S. Pat. No. 4,011,898, results in a catheter which exhibits severe discoloration. For example, a catheter made according to U.S. Pat. No. 4,923,450 which has a coating of the antibiotic zeolite material of U.S. Pat. No. 4,011,898 adhered to its surface becomes highly discolored within days.

A conventional catheter is typically comprised of a hydrophobic polymer. When antibiotic zeolite is incorporated in such a catheter, however, water is unable to reach the zeolite in the bulk of the material. The bulk of the zeolite is, therefore, ineffective against bacteria surrounding the catheter since only the zeolite at the surface of the catheter is active.

U.S. Pat. No. 5,305,827 describes an antimicrobial hydrophilic coating for heat exchangers. The coating includes silver oxide, to inhibit microbial growth and improve adhesion to the heat transfer surfaces of a heat exchanger. However, this coating exhibits severe discoloration and is typically antimicrobially effective for 3 days or less.

Japanese Pat. Application No. 03347710 relates to a non-woven fabric bandage containing synthetic fibers and hydrophilic fibers. The synthetic fibers contain zeolite which is ion-exchanged with silver, copper, or zinc ions.

U.S. Pat. No. 4,923,450 discloses incorporating zeolite in bulk materials. When zeolite is conventionally compounded into polymers, however, the zeolite often aggregates, causing poor dispersion of the zeolite in the polymer. When such material is molded or extruded, the surface of the polymer is frequently beaded instead of flat. Poor dispersion of the zeolite also can cause changes in the bulk properties of the polymer, such as a reduction in tensile strength. Any significant changes in the bulk properties of medical devices, such as catheters, however, result in a need to seek regulatory clearance by the U.S. Food and Drug Administration (FDA), which is a costly and time consuming process.

Furthermore, it has been found by the present inventors that conventionally kneading antibiotic zeolites in many polymeric materials results in a "hazy" appearance and in discoloration. This appears also to result from inadequate dispersion of the zeolite, i.e., the formation of zeolite aggregates in the material, and the inclusion of air or water during the kneading process.

U.S. Pat. No. 4,938,958 describes antibiotic zeolites in which a portion of the ion-exchangeable ions in the zeolite are replaced with amnmonium. This results in a product which exhibits reduced discoloration. However, as described in U.S. Pat. No. 4,938,955, it is often necessary to add an organic discoloration inhibitor, in addition to the antibiotic zeolite, to adequately prevent discoloration of the resin in which the zeolite is incorporated. Discoloration inhibitors are often not biocompatible and cannot be incorporated into medical devices. Furthermore, incorporation of an organic discoloration inhibitor in the polymeric material of a medical device may cause changes in the bulk properties of the material that are highly undesirable.

Therefore, there is a need for a hydrophilic polymer coating which contains an antimicrobial material which releases antibiotic metal ions and avoids antibiotic particle aggregation. Furthermore, there is a need for a hydrophilic polymer coating which contains an antimicrobial material which does not discolor.

SUMMARY OF THE INVENTION

The invention relates to a substrate having an antibiotic coating composition coated thereon. The coating composition is formed of a hydrophilic polymer having antibiotic ceramic particles dispersed therein, preferably, without substantial aggregation of the particles.

Also, an article is provided comprising a substrate on which is coated an antibiotic hydrophilic coating composition. The coating composition comprises a hydrophilic polymer having antibiotic ceramic particles dispersed therein.

In another embodiment, the invention relates to a coating solution comprising a hydrophilic polymer having antibiotic zeolite particles dispersed therein and an organic solvent.

Yet another embodiment of the invention is a method for preparing an antibiotic hydrophilic coating on a substrate. The method involves applying an antibiotic hydrophilic coating solution comprising a hydrophilic polymer, dispersed antibiotic ceramic particles, and an organic solvent, to the substrate.

DETAILED DESCRIPTION OF THE INVENTION

Figure 1:
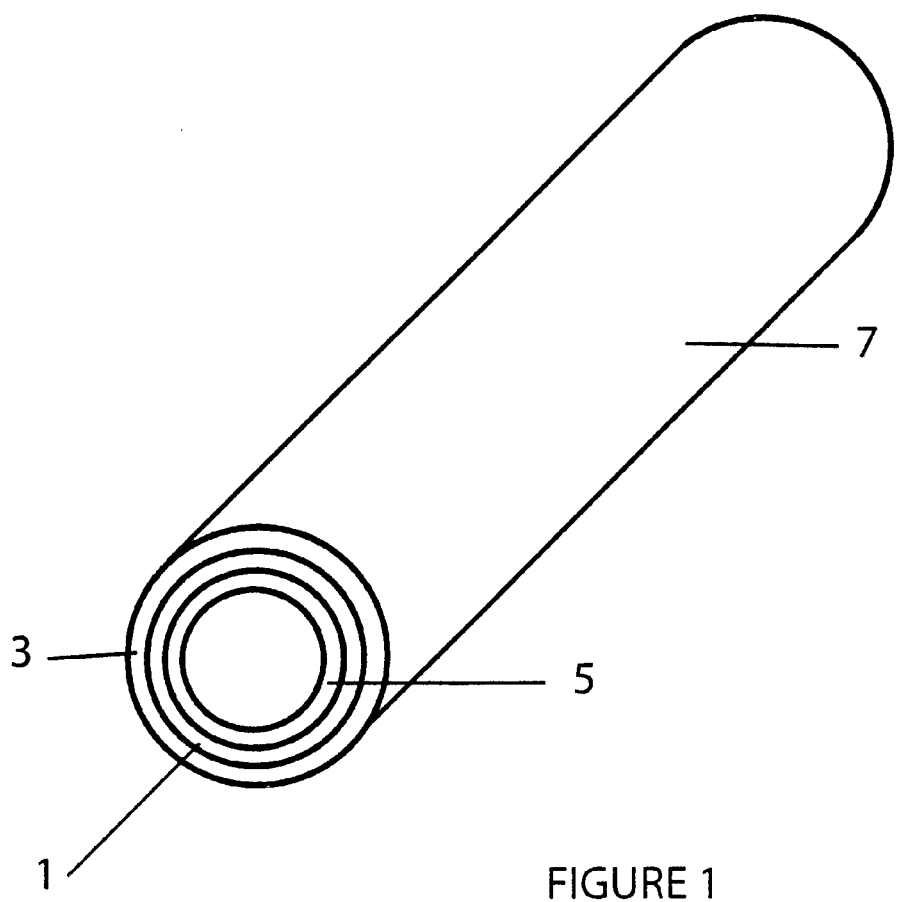
FIG. 1 shows a catheter having an antibiotic hydrophilic coating thereon according to the invention.

All patent applications, patents, patent publications, and literature references cited in this specification are hereby incorporated by reference in their entirety. In the case of inconsistencies, the present description, including definitions, is intended to control.

According to the present invention, an antibiotic hydrophilic composition is used to coat a substrate. The composition contains a hydrophilic polymer having antibiotic ceramic particles dispersed therein.

Antibiotic ceramic particles include, but are not limited to, zeolites, hydroxyapatite, zirconium phosphates and other ion-exchange ceramics. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717; and 5,405,644. Preferably, antibiotic zeolite is employed containing ion-exchanged antibiotic metal ions.

The coating preferably has a thickness of from about 0.1 $\mu$m to about 5 mm, more preferably, from about 0.5 $\mu$m to about 100 $\mu$m and, most preferably, from about 1 to about 50 $\mu$m. As will be appreciated by those skilled in the art, however, the optimal thickness of coating employed will depend on the substrate being coated.

Any suitable hydrophilic polymer may be employed, including, for example, polyhydroxyethyl methacrylate, polyacrylamide, polydimethylsiloxane, N-vinyl-2-pyrrolidinone, hydrophilic polyurethane, and the like. Preferably, the hydrophilic polymer is hydrophilic polyurethane, such as the TECOPHILIC™ polyurethane sold by Thermedics of Woburn, Mass.

An amount of antibiotic ceramic is dispersed in the hydrophilic polymer that is effective to release the antibiotic metal ions in a microbiocidally effective amount. In medical device embodiments of the present invention, the coating preferably exhibits a release rate ranging from about 5 to about 50 ppb of microbiocidally effective silver ions upon contact of the medical device with body tissues or when contaminated outside of the body with, e.g., microbes transferred from uncovered hands, for a period of more than 1 week.

In antibiotic zeolite particles used in the preferred embodiment of the present invention, ion-exchangeable ions present in zeolite, such as sodium ions, calcium ions, potassium ions and iron ions are partially replaced with ammonium and antibiotic metal ions. Such ions may co-exist in the antibiotic zeolite particle since they do not prevent the bacteriocidal effect. Examples of antibiotic metal ions include, but are not limited to, ions of silver, copper, zinc, mercury, tin, lead, bismuth, cadmium, chromium and thallium. Preferably, the antibiotic metal ions are silver, copper or zinc ions, and most preferably silver is employed. These antibiotic metal ions may be incorporated into the zeolite by themselves or in a mixture.

The antibiotic metal ion is preferably present in the range of from about 0.1 to about 15 wt % of the zeolite based upon 100% total weight of zeolite. In one embodiment, the zeolite contains from about 0.1 to about 15 wt % of silver ions and from about 0.1 to about 8 wt % of copper or zinc ions. Although ammonium ion may be contained in the zeolite at a concentration as high as about 20 wt % or less of the zeolite, it is desirable to limit the content of ammonium ions to about 0.5 to about 2.5 wt % of the zeolite, more preferably from about 0.5 to about 2.0 wt %, and most preferably, from 0.5 to about 1.5 wt %.

Antibiotic zeolites, including the antibiotic zeolites disclosed in U.S. Pat. No. 4,938,958, are well-known and may be prepared for use in the present invention using known methods. These include the antibiotic zeolites disclosed in U.S. Pat. No. 4,938,958.

Either natural zeolites or synthetic zeolites may be used to prepare the antibiotic zeolites used in the present invention. "Zeolite" is an aluminosilicate having a three dimensional skeletal structure that is represented by the formula: $XM_2/nO\text{—}Al_2O_3\text{—}YSiO_2\text{—}ZH_2O$. M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite= 11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antibiotic metal ions.

The specific surface area of preferred zeolite particles is preferably at least 150 m$^2$/g (anhydrous zeolite as standard) and the $SiO_2/Al_2O_3$ mole ratio in the zeolite composition is preferably less than 14 and more preferably less than 11.

The antibiotic metal ions used in the antibiotic zeolites should be retained on the zeolite particles through an ion-exchange reaction. Antibiotic metal ions which are adsorbed or attached without an ion-exchange reaction exhibit a decreased bacteriocidal effect and their antibiotic effect is not long-lasting. Nevertheless, it can be advantageous for imparting quick antimicrobial action to maintain a sufficient amount of surface adsorbed metal ion.

In the ion-exchange process, the antibiotic metal ions tend to be converted into their oxides, hydroxides, and basic salts either in the micropores or on the surfaces of the zeolite and also tend to deposit there, particularly when the concentration of metal ions in the vicinity of the zeolite surface is high. Such deposition tends to adversely affect the bacteriocidal properties of ion-exchanged zeolite.

In an embodiment of the antibiotic zeolites, a relatively low degree of ion exchange is employed to obtain superior bacteriocidal properties. It is believed to be required that at least a portion of the zeolite particles retain metal ions having bacteriocidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

A preferred antibiotic zeolite for use in the invention is type A zeolite containing either a combination of ion-exchanged silver, zinc, and ammonium or silver and ammonium. One such zeolite is manufactured by Shinagawa, Inc. under the product number AW-10N and consists of 0.6% by weight of of silver ion-exchanged in Type A zeolite particles having a diameter of about 2.5 $\mu$m. Another formulation, AJ-10N, consists of about 2% by weight of silver ion-exchanged in Type A zeolite particles having a diameter of about 2.5 $\mu$m. Yet another formulation, AW-80, contains 0.6% by weight of silver ion-exchanged in Type A zeolite particles having a diameter of about 1.0 $\mu$m. Another formulation, AJ-80N, consists of about 2% by weight of silver ion-exchanged in Type A zeolite particles having a diameter of about 1.0 $\mu$m. These zeolites preferably contain between about 0.5% and 2.5% by weight of ion-exchanged ammonium. The zeolites are often obtained in master batches of low density polyethylene, polypropylene, or polystyrene, containing 20 wt % of the zeolite.

A discoloration agent may be added to the antibiotic hydrophilic polymer. Preferably, the discoloration agent is biocompatible. Preferred discoloration agents include, but are not limited to, inorganic discoloration inhibitors such as ammonium. More preferably, the inorganic discoloration inhibitor is an ion-exchanged ammonium ion in the antibiotic zeolite. The antibiotic hydrophilic polymer is preferably substantially free of organic discoloration inhibitors.

The antibiotic hydrophilic polymer preferably is also substantially free of aggregates of antibiotic zeolite. Substantial aggregation of the antibiotic zeolite may be prevented by dispersion of the zeolite in the hydrophilic polymer using standard compounding techniques.

The antibiotic hydrophilic polymer preferably contains from about 0.05 to about 10% by weight of antibiotic zeolite based upon 100% total weight of antibiotic hydrophilic polymer. More preferably, the polymer contains from about 0.1% to about 5% by weight of antibiotic zeolite and, most preferably, from about 0.1% to about 1% by weight of antibiotic zeolite.

The substrate employed in accordance with the invention may be any substrate to which the hydrophilic polymer adheres, including, but not limited to, glass, plastic (such as polyurethane, polyethylene, polyvinyl chloride, and polypropylene), metal (such as aluminum, copper, bronze, and stainless steel), and woven and non-woven fabrics.

According to another embodiment of the invention, an article is provided comprising a substrate on which is coated the antibiotic hydrophilic coating. The article may be a medical article, such as a catheter, stent, heart valve, or vascular graft, a component of a heat exchanger, such as the tank, a building product, such as paper, house wrap, or shingles, or a water transport or storage product, such as a pipe or tank liner.

In one embodiment, the coating of the present invention forms an outer and/or inner surface of a medical catheter. Preferably, as shown in FIG. 1, the catheter 1 is coated with the antimicrobial hydrophilic coating, on both the outside 3 and inside 5 of the catheter to form a coated catheter 7. The hydrophilic polymer absorbs water, thereby drawing the antibiotic ions in the polymer to the surface of the catheter. Thus, zeolite embedded in the bulk of the polymer is effective against bacteria on the catheter surface. Preferably, the thickness of the coating on the catheter is from about 0.5 to about 100 $\mu$m and, more preferably, from about 1 to about 50 $\mu$m.

A coating solution is also provided according to the invention which contains the hydrophilic polymer having antibiotic ceramic particles dispersed therein in an organic solvent. Any organic solvent which dissolves the hydrophilic polymer may be employed. Preferred solvents include tetrahydrofuran, dimethylacetamide, methylethylketone, and mixtures thereof.

The coating solution preferably contains from about 0.01 to about 50% by weight solids based upon 100% total weight of the coating solution. More preferably, the coating solution contains from about 0.1 to about 30% by weight solids and, most preferably, from about 1 to about 20% by weight solids.

The solids in the coating solution preferably contain from about 0.01 to about 90% by weight of antibiotic zeolite and from about 10% to about 99.99% by weight of hydrophilic polymer based upon 100% total weight solids. More preferably, the solids comprise from about 0.05 to about 80% by weight of antibiotic zeolite and from about 20% to about 99.95% by weight of hydrophilic polymer. Most preferably, the solids comprise from about 0.1 to about 70% by weight of antibiotic zeolite and from about 30% to about 99.9% by weight of hydrophilic polymer.

The coating solution of the invention may be prepared by first dispersing antibiotic zeolite into the hydrophilic polymer. Any suitable method of dispersion, but preferably high shear mixing with a dual screw compounder, is performed. The hydrophilic polymer containing the dispersed antibiotic particles is then dissolved in the organic solvent.

Another suitable method for preparing the antibiotic coating solution of the invention is as follows. Antibiotic zeolite in an effective amount is dispersed into an organic solvent to form a first solution. The hydrophilic polymer is dissolved in an organic solvent to form a second solution, preferably by mixing the polymer into the solvent at about 20° C. to about 70° C., more preferably, from about 25° C. to about 60° C. and, most preferably, from about 40° C. to about 60° C. The heating is performed in an explosion proof container. The concentration of solvent in the second solution preferably ranges from about 0% to about 20% by weight, more preferably, from about 0% to about 15% and, most preferably, from about 0% to about 10%. The first solution and second solution are then mixed to form the antibiotic coating solution of the invention.

The antibiotic hydrophilic coated substrate is prepared by applying the antibiotic hydrophilic coating solution to the substrate. Preferably, the contact time of the coating solution with a polymeric substrate is minimized, since the solvent of the coating solution may dissolve the polymeric substrate. The coating time, however, should be sufficient to adhere the coating to the substrate. Suitable methods of applying the coating solution to the substrate include, but are not limited to, dipping and spraying. Dipping is preferred. Preferably, when the coating solution is applied, the antibiotic ceramic particles are maintained in suspension in the solution.

A primer may be applied to the substrate before applying the solution polymer to help bond the hydrophilic polymer to the substrate.

If zeolite is not adequately dispersed in the hydrophilic polymer, the zeolite clumps and adheres to polymeric particles. Coatings produced without adequate dispersion in the hydrophilic polymer exhibit low efficacy against bacterial and fungal cells and poor adherence to substrates. Clumping of the antibiotic zeolite powder also results in discoloration of the coating.

The antibiotic properties of the antibiotic zeolite particles of the invention may be assayed using conventional assay techniques, including for example determining the minimum growth inhibitory concentration (MIC) with respect to a variety of bacteria, eumycetes and yeast. In such a test, the bacteria listed below may be employed:

Bacillus cereus var mycoides,
Escherichia coli,
Pseudomonas aeruginosa,
Staphylococcus aureus,
Streptococcus faecalis,
Aspergillus niger,
Aureobasiduim pullulans,
Chaetomium globosum,
Gliocladium virens,
Penicillum funiculosum,
Candida albicans,
Saccharomyces cerevisiae, The assay for determining MIC can be carried out by smearing a solution containing bacteria for inoculation onto a plate culture medium.

The present invention will hereunder be explained in more detail with reference to the following non-limiting working examples.

EXAMPLE 1

A 1"×1" sample of knitted polyester, available from Bard Vascular Systems Division as knitted polyester style no. 6103, was coated with the antibiotic hydrophilic coating of the present invention as follows.

A coating solution containing 2.90% by weight of hydrophilic polyurethane sold under the trademark Tecophilic™ from Thermedics of Woburn, Mass.; 96.81% tetrahydrofuran; and 0.29% AW-10N zeolite, available from Shinagawa, Inc., was prepared and mixed with a high shear mixer.

An eye dropper was used to apply the coating solution to the polyester sample. The polyester sample was then sprayed with air to remove excess powder and to cure the coating.

EXAMPLE 2

A Dow Shaker Test was performed on the polyester sample prepared in Example 1 (hereafter referred to as Sample A) to determine its inhibitory effect against *S. aureus*. The Dow Shaker Test is based on Dow Corporate Test Method 0923 for testing aerobic bacteria by Dow Chemical. The Dow Shaker Test is described below.

Sample A was sterilized at 121° C. for 15 minutes.

A culture tube containing *S. aureus* was prepared by adding one disk of *S. aureus* to the culture tube. From about 2 to 5 ml of broth was added to the culture tube. Then the culture tube was agitated with a vortex mixer until the disk was completely dissolved in the broth. The bacteria in the culture tube was incubated for at least 3 hours at 35° C. The culture tube was then refrigerated at about 2–8° C. until needed for testing.

A 5 ml sample of bacteria from the culture tube was removed and agitated in a vortex mixer. The absorbance of the sample was measured at 475 nm with a spectrophotometer relative to the absorbance of the aforementioned broth. Broth and/or bacteria from the culture tube were added to the sample until an absorbance of about 0.1 absorbance units was obtained. This corresponds to from about $10^5$ to about $10^6$ colony forming units per milliliter (CFU/ml).

5 ml of suspension was extracted from the sample and added to a flask containing 70 ml of sterile buffer. The resulting solution contained from about $10^4$ to about $10^5$ CFU/ml. The flask was capped and shaken on a wrist action shaker for 1 minute at maximum speed. This is referred to as time "0 hours" below.

The number of colony forming units in 1 ml of the solution was determined at time 0 hours by the following procedure. 1 ml of solution was extracted from the flask and added to a vial containing 9 ml of buffer solution to form a 10:1 dilution. The solution was repeatedly diluted with buffer solution until a plate count of about 30 to about 200 CFU/ml was obtained.

1 ml of the solution from the flask and each dilution were transferred to separate petri dishes. About 15 to 20 ml of molten agar was added to each dish. Each dish was rotated 10 times clockwise and 10 times counter-clockwise to evenly distribute the agar and bacteria. Then each dish was incubated for 18–24 hours at 35° C. A plate count was performed on the petri dish containing from about 30 to about 200 bacteria colony forming units to determine the number of colony forming units.

Also, at time 0 hours, sample A was added to the flask and shaken with a wrist action shaker for 1 hour. The number of colony forming units in 1 ml of the solution in the flask was determined by the above procedure using 2 petri dishes. If the numbers of colony forming units in the 2 petri dishes were not within 15% of each other, the entire Dow Shaker Test was repeated.

The number of colony forming units in 1 ml of the solution was also determined after shaking the flask with a wrist action shaker for 18 and 24 hours.

A control was tested by the same procedure as sample A. The control was an untreated 1"×1" sample of no. 6103 polyester.

The numbers of colony forming units measured at 0 hours, 1 hour, 18 hours, and 24 hours for sample A and the control are shown in Table 1. The percentages of bacteria killed by sample A and the control at times 1 hour, 18 hours, and 24 hours are shown in Table 2.

TABLE 1

| | Bacteria Counts of *S. aureus* (Colony Forming Units) | | | |
|---|---|---|---|---|
| Sample | 0 hours | 1 hour | 18 hours | 24 hours |
| Sample A | 780,000 | 2,145,000 | 85,000 | 3,700 |
| Control | 480,000 | 12,400,00 | 4,720,00 | 4,300,000 |

TABLE 2

| | % Killed | | |
|---|---|---|---|
| Sample | 1 hour | 18 hours | 24 hours |
| Sample A | 0 | 89.10% | 99.53% |
| Control | 0 | 0 | 0 |

As indicated in Table 2, Sample A exhibited 99.53% inhibition of *S. aureus* after 24 hours of contact with the bacteria.

EXAMPLE 3

SAFETY AND BIOCOMPATIBILITY

Safety and biocompatibility tests were conducted on the antibiotic zeolites employed in the invention. ISO 10993-1 procedures were employed. The following results were obtained:

Cytotoxicity: Non-Toxic
Acute Systemic Toxicity: Non-Toxic
Intracutaneous Toxicity: Passed
Skin Irritation Test: Non-Irritant
Chronic Toxicity: No Observable Effect
In-vitro Hemolysis: Non-Hemolytic
30-day Muscle Implant Test: Passed
60-day Muscle Implant Test: Passed
90-day Muscle Implant Test: Passed
Ames Mutagenicity Test: Passed
Pyrogenicity: Non-Pyrogenic Thus, the antibiotic zeolites are exceptionally suitable under relevant toxicity and biocompatibility standards for use in articles coated with the antibiotic zeolites.

While preferred embodiments of the invention have been described in the foregoing examples, it will be understood by those skilled in the art that various changes and modifications may be made therein without departing from the spirit and the scope of the invention. Accordingly, the above description should be construed as illustrating and not limiting the scope of the invention.

What is claimed is:

1. An antibiotic coating solution comprising a hydrophilic polymer having antibiotic ceramic particles dispersed therein and an organic solvent wherein the hydrophilic polymer is selected from the group consisting of polyhydroxyethyl methacrylate, polyacrylamide, N-vinyl-2-pyrrolidinone, and hydrophilic polyurethane and the antibiotic ceramic particles comprise ion-exchanged antibiotic metal ions.

2. An antibiotic coating solution according to claim 1, wherein the antibiotic ceramic particles are selected from the group consisting of ion-exchanged zeolite, hydroxyapatite, and zirconium phosphate.

3. An antibiotic coating solution according to claim 2, wherein the antibiotic ceramic particles are ion-exchanged zeolite.

4. An antibiotic coating solution according to claim 3, wherein said ion-exhanged zeolite comprises an antibiotic metal ion selected from the group consisting of silver, copper, zinc, mercury, tin, lead, bismyth, bismutin, cadmium, chromium and thallium.

5. An antibiotic coating solution according to claim 1, wherein said ion-exchanged ceramic particles comprise an antibiotic metal ion selected from the group consisting of silver, copper, zinc, mercury, tin, lead, bismyth, bismutin, cadmium, chromium and thallium.

6. An antibiotic coating solution according to claim 1, wherein said polymer further comprises an inorganic discoloration agent.

7. An antibiotic coating solution according to claim 6, wherein said inorganic discoloration agent is ammonium.

8. An antibiotic coating solution according to claim 3, wherein said antibiotic zeolite further comprises ion-exchanged ammonium ions.

9. An antibiotic coating solution according to claim 1, wherein said organic solvent is selected from a group consisting of tetrahydrofuran, dimethylacetamide, methylethylketone, and mixtures thereof.

10. An antibiotic coating solution according to claim 1, wherein said coating solution comprises from about 0.01 to about 50% by weight solids.

11. An antibiotic coating solution according to claim 10, wherein said coating solution comprises from about 0.1 to about 30% by weight solids.

12. An antibiotic coating solution according to claim 11, wherein said coating solution comprises from about 1 to about 20% by weight solids.

13. An antibiotic coating solution according to claim 1, having a content of solids therein, wherein the antibiotic ceramic particles constitute a portion of the solids and the solids of said coating solution comprised from about 0.01 to about 90% by weight of antibiotic zeolite.

14. An antibiotic coating solution according to claim 13, wherein the solids of said coating solution comprise from about 0.05 to about 80% by weight of antibiotic zeolite.

15. An antibiotic coating solution according to claim 14, wherein the solids of said coating solution comprise from about 0.1 to about 70% by weight of antibiotic zeolite.

16. An antibiotic coating solution according to claim 1, having a content of solids therein, wherein the antibiotic ceramic particles constitute a portion of the solids, and the solids of said coating solution comprised from about 10 to about 99.99% by weight of hydrophilic polymer.

17. An antibiotic coating solution according to claim 14, wherein the solids of said coating solution comprise from about 20 to about 99.95% by weight of hydrophilic polymer.

18. An antibiotic coating solution according to claim 17, wherein the solids of said coating solution comprise from about 30 to about 99.9% by weight of hydrophilic polymer.

* * * * *